(12) United States Patent
Trahan et al.

(10) Patent No.: US 12,134,798 B1
(45) Date of Patent: Nov. 5, 2024

(54) METHODS OF DETECTING A LEAK FROM A SUBARRAY OF A MICROARRAY CHIP, KITS OF COMPONENTS THAT FACILITATE LEAK DETECTION, AND MICROARRAY CHIPS CONFIGURED FOR LEAK DETECTION

(71) Applicant: SomaLogic Operating Co., Inc., Boulder, CO (US)

(72) Inventors: Rachel Woolaver Trahan, Arvada, CO (US); Jon H. Monserud, Golden, CO (US); Maarten Rutgers, Los Angeles, CA (US); Jason Cleveland, Boulder, CO (US); Barry Vant-Hull, Boulder, CO (US); Stephan Kraemer, Boulder, CO (US)

(73) Assignee: SomaLogic Operating Co., Inc., Boulder, CO (US)

( * ) Notice: Subject to any disclaimer, the term of this patent is extended or adjusted under 35 U.S.C. 154(b) by 0 days.

(21) Appl. No.: 18/530,860

(22) Filed: Dec. 6, 2023

(51) Int. Cl.
*C12Q 1/6837* (2018.01)
*B01L 3/00* (2006.01)

(52) U.S. Cl.
CPC ...... *C12Q 1/6837* (2013.01); *B01L 3/502761* (2013.01); *B01L 2200/0647* (2013.01); *B01L 2200/16* (2013.01); *B01L 2300/0654* (2013.01); *B01L 2300/0819* (2013.01); *B01L 2300/168* (2013.01)

(58) Field of Classification Search
CPC ...................... C12Q 1/6837; B01L 2300/0819
See application file for complete search history.

(56) References Cited

U.S. PATENT DOCUMENTS

| | | | |
|---|---|---|---|
| 2004/0126766 A1* | 7/2004 | Amorese | B01L 3/50853 435/6.12 |
| 2006/0073486 A1* | 4/2006 | Sana | C12Q 1/6837 435/6.12 |

* cited by examiner

*Primary Examiner* — Joseph G. Dauner
(74) *Attorney, Agent, or Firm* — Kolitch Romano Dascenzo Gates LLC

(57) ABSTRACT

Methods of detecting a leak from a subarray of a microarray chip, kits of components that facilitate leak detection, and microarray chips configured for leak detection are disclosed herein. The methods include positioning, within the given subarray, a sample solution, which includes dissolved sample molecules (DSMs) that define a dissolved sample oligonucleotide sequence and dissolved leak detection molecules (DLDMs) that define a predetermined dissolved leak detection oligonucleotide sequence. The methods also include detecting the DLDMs within a region of the microarray chip that is external the given subarray. The kits of components include the microarray chip and DLDMs. The microarray chips includes a plurality of subarrays and a leak detection region that is at least partially external the plurality of subarrays.

19 Claims, 10 Drawing Sheets

METHODS OF DETECTING A LEAK FROM A SUBARRAY OF A MICROARRAY CHIP, KITS OF COMPONENTS THAT FACILITATE LEAK DETECTION, AND MICROARRAY CHIPS CONFIGURED FOR LEAK DETECTION

FIELD OF THE DISCLOSURE

The present disclosure relates generally to methods of detecting a leak from a subarray of a microarray chip, to kits of components that facilitate leak detection, and to microarray chips configured for leak detection.

BACKGROUND

Microarray deoxyribonucleic acid (DNA) chips may be utilized to detect the presence and/or concentration of specific dissolved sample oligomers in a sample solution. Such microarray DNA chips generally include a plurality of subarrays, each of which includes a plurality of spots, or test features. Each test feature includes a large number of attached oligomers. Within each test feature, each attached oligomer has a specific oligomer sequence, and the specific oligomer sequence generally will vary from one test feature to the next.

Upon contact between the test features and the sample solution that includes sample oligomers, sample oligomers with an oligomer sequence that is complementary to a given test feature will hybridize with the attached oligomers of the given test feature, producing a double strand of DNA. In practice, the sample oligomers generally include a fluorophore, thereby permitting a fluorescence microscope to detect the presence, and degree, of hybridization for various test features within the microarray via detection of fluorescent light intensity from the various test features. This process enables identification of the sample oligomers.

A significant number of subarrays may be fabricated on a single slide, thereby permitting the simultaneous analysis of a number of different sample solutions. It is important to fluidically isolate the subarrays from one another to avoid cross-contamination, as leaks between subarrays generally will lead to mixing of sample oligomers and invalid results.

A number of different technologies may be utilized to fluidically isolate the subarrays from one another, including technologies with an interstitial void space between adjacent subarrays and technologies where a single barrier, such as a single gasket, separates adjacent subarrays. Technologies that include the interstitial void space may be less prone to subarray-to-subarray leaks; however, the use of this interstitial space leads to a decrease in the overall density of the subarrays on the slide. Technologies that utilize the single barrier are more prone to subarray-to-subarray leaks; however, they provide an increased subarray density on the slide. Should a leak occur, neither technology provides an independent methodology via which the leak may be detected, quantified, and/or evaluated. Thus, there exists a need for methods of detecting a leak between subarrays of a microarray chip, kits of components that facilitate leak detection, and microarray chips configured for leak detection.

SUMMARY

Methods of detecting a leak from a subarray of a microarray chip, kits of components that facilitate leak detection, and microarray chips configured for leak detection are disclosed herein. The methods include positioning, within the given subarray, a sample solution, which includes dissolved sample molecules (DSMs) that define a dissolved sample oligonucleotide sequence and dissolved leak detection molecules (DLDMs) that define a predetermined dissolved leak detection oligonucleotide sequence. The methods also include detecting the DLDMs within a region of the microarray chip that is external the given subarray.

The kits of components include a microarray chip and DLDMs. The microarray chip includes a substrate, a plurality of subarrays formed on the substrate, a perimeter sealing structure configured to form a fluid seal with the substrate, and a leak detection region. Each subarray of the plurality of subarrays includes a plurality of test features, and wherein each test feature of the plurality of test features includes anchored test molecules (ATMs), which are anchored to the substrate and define a predetermined anchored test oligonucleotide sequence. The perimeter sealing structure and the substrate together define a fluid-receiving well of each subarray, and the perimeter sealing structure is configured to fluidically isolate each subarray from all other subarrays of the plurality of subarrays. The leak detection region includes anchored leak detection molecules (ALDMs), which are attached to the substrate and define a predetermined anchored leak detection oligonucleotide sequence. The kits also include dissolved leak detection molecules (DLDM), which are configured to be dissolved within a sample solution for the given subarray and define a predetermined dissolved leak detection oligonucleotide sequence that is complementary to the predetermined anchored leak detection oligonucleotide sequence.

The microarray chips include a substrate, a plurality of subarrays formed on the substrate, a perimeter sealing structure configured to form a fluid seal with the substrate, and a leak detection region. Each subarray includes a plurality of test features, and each test feature of the plurality of test features includes anchored test molecules (ATMs), which are anchored to the substrate and define a predetermined anchored test oligonucleotide sequence. The perimeter sealing structure and the substrate together define a fluid-receiving well of each subarray, and the perimeter sealing structure is configured to fluidically isolate each subarray from all other subarrays of the plurality of subarrays. The leak detection region includes anchored leak detection molecules (ALDMs), which are attached to the substrate and define a predetermined anchored leak detection oligonucleotide sequence. The leak detection region is external to all subarrays of the plurality of subarrays and/or positioned within a contact region between the perimeter sealing structure and the substrate.

Definitions

As used herein, the phrase "deoxyribonucleic acid" and the corresponding acronym "DNA" refer to an oligomer, or a polymer, that includes a polynucleotide chain. This oligomer, or polymer, chain defines a specific oligonucleotide sequence that carries genetic information. Two of these chains may be coiled together, or may hybridize, to form a double helix.

As used herein, the phrase "oligonucleotide sequence" refers to a sequence, or an order, of nucleotides, or bases, within the corresponding molecule. Examples of nucleotides, or bases, include adenine (A), guanine (G), cytosine (C), thymine (T), and uracil (U), with thymine only naturally occurring in DNA and uracil only naturally occurring in ribonucleic acid (RNA).

As used herein, the phrase "dissolved sample molecules" and the corresponding acronym "DSMs" refer to oligomers that are dissolved within a sample solution and that define a (generally unknown) sample oligonucleotide sequence. Stated differently, DSMs refer to molecules for which it may be desirable to ascertain the sample oligonucleotide sequence and/or to determine whether or not the sample oligonucleotide sequence corresponds to one or more specific and/or predetermined test oligonucleotide sequences.

As used herein the phrase "dissolved leak detection molecules" and the corresponding acronym "DLDMs" refer to oligomers that are dissolved within the sample solution and that define a (generally known) predetermined dissolved leak detection oligonucleotide sequence. DLDMs are included within the sample solution to permit and/or facilitate leak detection, as is discussed in more detail herein.

As used herein the phrase "microarray chip" refers to a device that is utilized to determine whether or not a particular DSM includes one or more specific and/or predetermined test oligonucleotide sequences. Microarray chips may be utilized to determine a concentration of the DSMs within the sample solution, to identify the sample oligonucleotide sequence of the DSMs, and/or to determine whether or not the sample oligonucleotide sequence of the DSMs is complementary to the one or more predetermined test oligonucleotide sequences on the microarray chip. This may be accomplished via hybridization between the DSMs and the predetermined test oligonucleotide sequences followed by direct and/or indirect detection of this hybridization. As discussed in more detail herein, microarray chips include a substrate, a plurality of subarrays formed on the substrate, and a perimeter sealing structure.

As used herein, the term "substrate" refers to any suitable material that defines a surface on which the plurality of subarrays may be formed. More specific examples of the substrate are disclosed herein.

As used herein, the term "subarray" refers to a plurality, or an array, of test features formed on the substrate. Each test feature includes a plurality anchored test molecules (ATMs), and detection of hybridization between the DSMs and a specific test feature may be utilized to determine the sample oligonucleotide sequence of the DSMs. In particular, the plurality of ATMs within a given test feature generally will have a single and/or a specific predetermined anchored test oligonucleotide sequence. In addition, each test feature generally will have a different single and/or specific predetermined anchored test oligonucleotide sequence when compared to each other test feature. As such, detection of hybridization between the DSMs and the ATMs of the given test feature indicates that the sample oligonucleotide sequence of the DSMs is complementary to the predetermined test oligonucleotide sequence of the ATMs within the given test feature. Microarray chips generally include the plurality of subarrays to permit and/or facilitate simultaneous testing of a plurality of different sample solutions.

As used herein, the phrase "perimeter sealing structure" refers to a structure that is configured form a fluid seal with the substrate such that perimeter sealing structure and the substrate together define a corresponding fluid-receiving well for each subarray. Stated differently, the perimeter sealing structure may fluidically isolate each subarray from each other subarray, thereby permitting and/or facilitating simultaneous testing of the plurality of different sample solutions by the plurality of subarrays. Examples of the perimeter sealing structure are disclosed herein.

As discussed in more detail herein, the perimeter sealing structure may, at times, leak. Such a leak may permit the sample solution from one subarray to leave that subarray, thereby representing a potential for cross-contamination among the plurality of subarrays. While it may not be feasible to completely eliminate the potential for leaks, microarray chips according to the present disclosure also include a leak detection region. As used herein, the phrase "leak detection region" refers to a region of the microarray chips that is at least partially external a given subarray and is utilized to detect the leak from the given subarray. In particular, the leak detection region includes anchored leak detection molecules (ALDMs) that define a predetermined anchored leak detection oligonucleotide sequence. The predetermined anchored leak detection oligonucleotide sequence is complementary to the predetermined dissolved leak detection oligonucleotide sequence of the DLDMs. As such, the ALDMs and the DLDMs will hybridize with one another upon contact therebetween, and detection of this hybridization is utilized to indicate the presence of the leak.

As is known to those of ordinary skill in the art, two oligonucleotide molecules will hybridize with one another when their oligonucleotide sequences are complementary to one another. Stated differently, and in DNA, the two oligonucleotide molecules will hybridize when their corresponding oligonucleotide sequences are such that adenine and thymine always pair with one another and also such that guanine and cytosine always pair with one another. This fact is utilized in microarray chips according to the present disclosure. In particular, hybridization is utilized to facilitate identification of DSMs via detecting hybridization between the DSMs and corresponding ATMs that are complementary thereto. In addition, hybridization is utilized to detect a leak via detecting hybridization between DLDMs and ALDMs that are complementary thereto.

DETAILED DESCRIPTION

Figure 1:
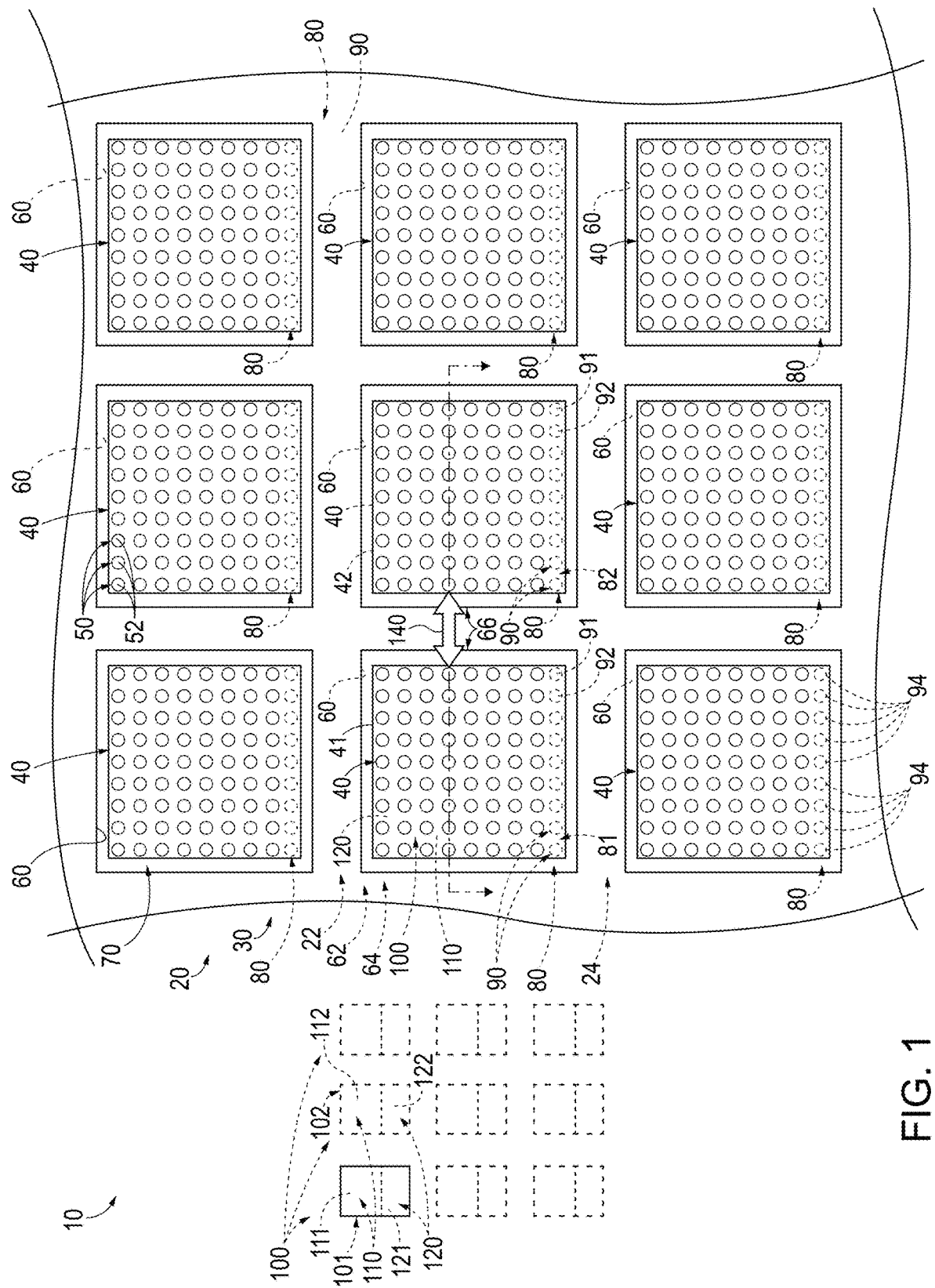
FIG. 1 is a schematic illustration of examples of microarray chips and sample solutions that may be included in kits, according to the present disclosure.

FIGS. 1-10 provide examples of microarray chips 20, of sample solutions 100, of kits 10 that include the microarray chips and the sample solutions, and/or of methods 200, according to the present disclosure. Elements that serve a similar, or at least substantially similar, purpose are labeled with like numbers in each of FIGS. 1-10, and these elements may not be discussed in detail herein with reference to each of FIGS. 1-10. Similarly, all elements may not be labeled in each of FIGS. 1-10, but reference numerals associated therewith may be utilized herein for consistency. Elements, components, and/or features that are discussed herein with reference to one or more of FIGS. 1-10 may be included in and/or utilized with any of FIGS. 1-10 without departing from the scope of the present disclosure.

In general, elements that are likely to be included in a particular embodiment are illustrated in solid lines, while elements that are optional are illustrated in dashed lines. However, elements that are shown in solid lines may not be essential to all embodiments and, in some embodiments, may be omitted without departing from the scope of the present disclosure.

FIG. 1 is a schematic illustration of examples of microarray chips 20 and sample solutions 100 that may be included in kits 10, according to the present disclosure. FIGS. 2-5 are schematic illustrations of examples of the microarray chip of FIG. 1 taken along line A-A of FIG. 1, and FIGS. 6-9 are additional schematic illustrations of examples of the microarray chip of FIG. 1 taken along line A-A of FIG. 1.

As collectively illustrated by FIGS. 1-9, microarray chips 20, which also may be referred to herein as chips 20, as microarray DNA chips 20, and/or as microarray RNA chips 20, include a substrate 30 and a plurality of subarrays 40 formed on the substrate. Each subarray 40 includes a plurality of test features 50, and each test feature 50 includes a plurality of anchored test molecules (ATMs) 52. ATMs 52 are anchored to substrate 30 and define a predetermined anchored test oligonucleotide sequence. The predetermined anchored test oligonucleotide sequence of ATMs 52 within each test feature 50 may differ from the predetermined test oligonucleotide sequence of at least one, a majority, or even all other test features of the plurality of test features. Stated differently, and in some examples, each test feature may define a unique predetermined anchored test oligonucleotide sequence.

Chips 20 also include a perimeter sealing structure 60 that is configured to form a fluid seal 62 with substrate 30, such as within a contact region 64 between the perimeter sealing structure and the substrate. Perimeter sealing structure 60 and substrate 30 together define, or at least partially define, a fluid-receiving well 70 of each subarray 40, and perimeter sealing structure 60 is configured to fluidically isolate each subarray 40 from all other subarrays of chip 20.

Chips 20 also include at least one leak detection region 80. Leak detection region 80 includes anchored leak detection molecules (ALDMs) 90 that are attached to substrate and define a predetermined anchored leak detection oligonucleotide sequence. The predetermined anchored leak detection oligonucleotide sequence may differ from the predetermined anchored test oligonucleotide sequence of every test feature 50. As discussed in more detail herein, and in some examples, one or more leak detection regions 80 may be positioned within subarrays 40, or within each subarray 40. Additionally or alternatively, and in some examples, one or more leak detection regions 80 may be positioned external subarrays 40, or external all subarrays 40, such as within an unwetted region 22 of chips 20.

Figure 2:
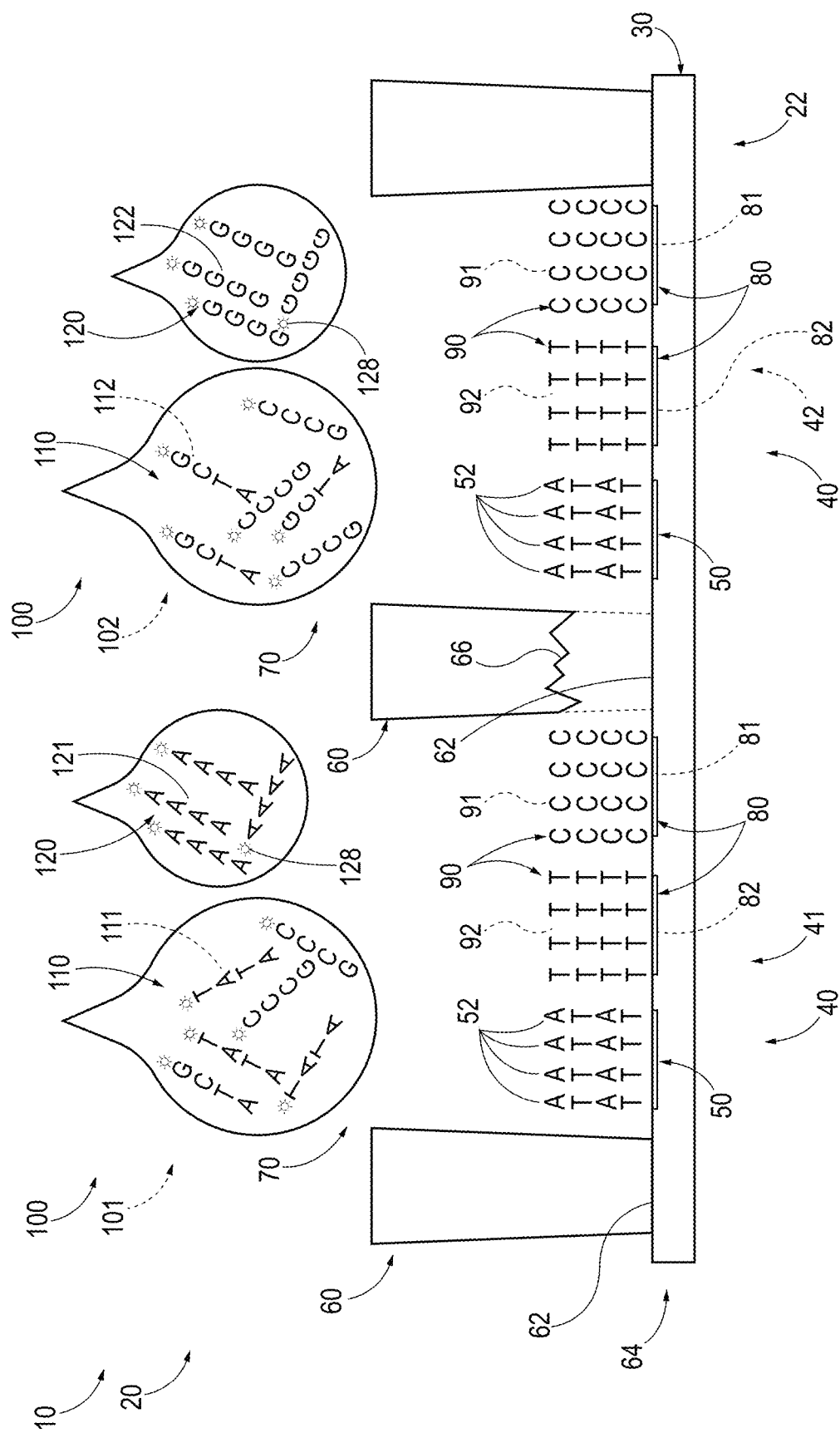
FIG. 2 is a schematic illustration of examples of the microarray chip of FIG. 1 taken along line A-A of FIG. 1 and prior to introduction of a sample solution.
Figure 3:
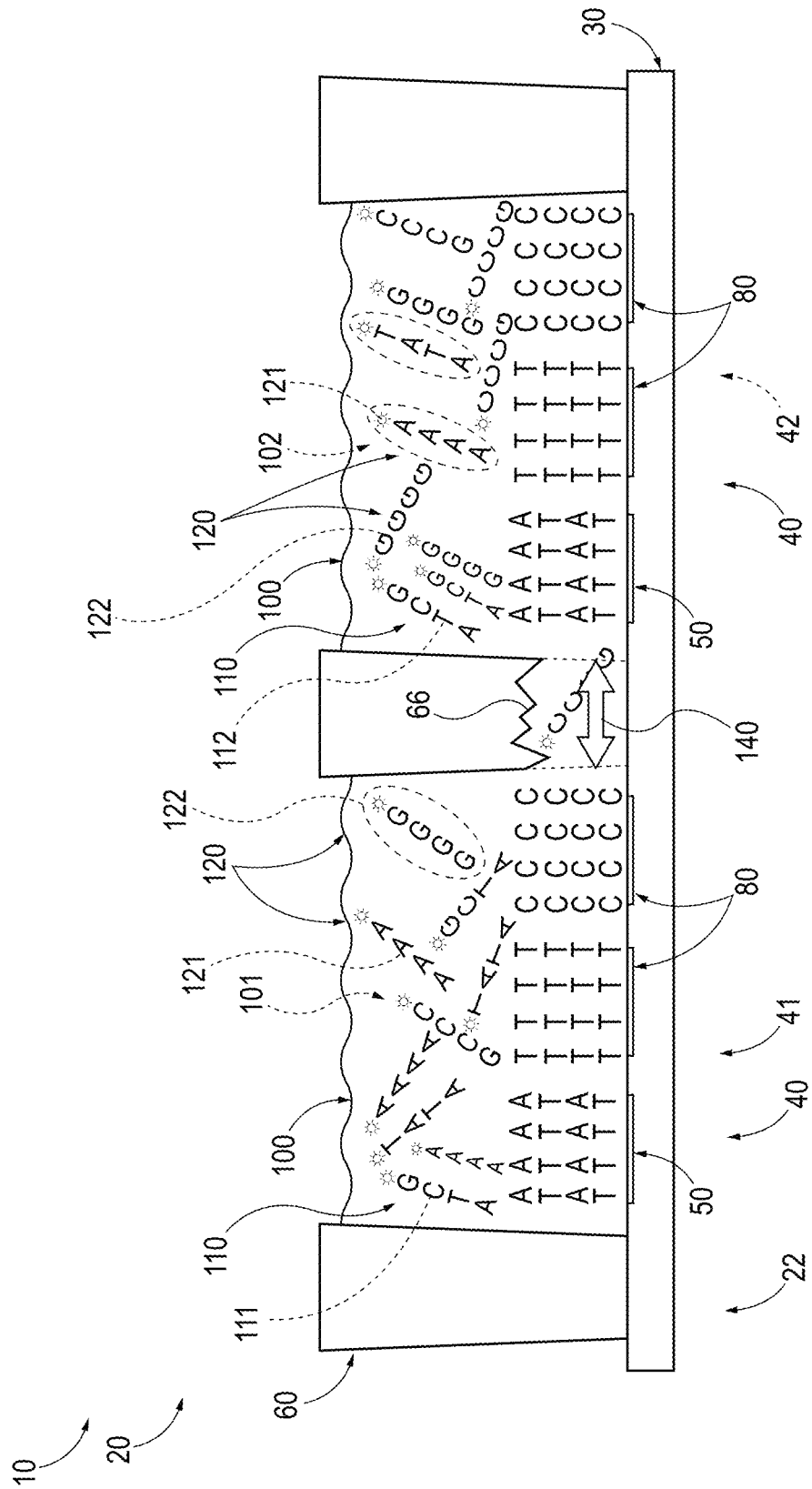
FIG. 3 is a schematic illustration of the microarray chip of FIG. 2 subsequent to introduction of the sample solution.
Figure 6:
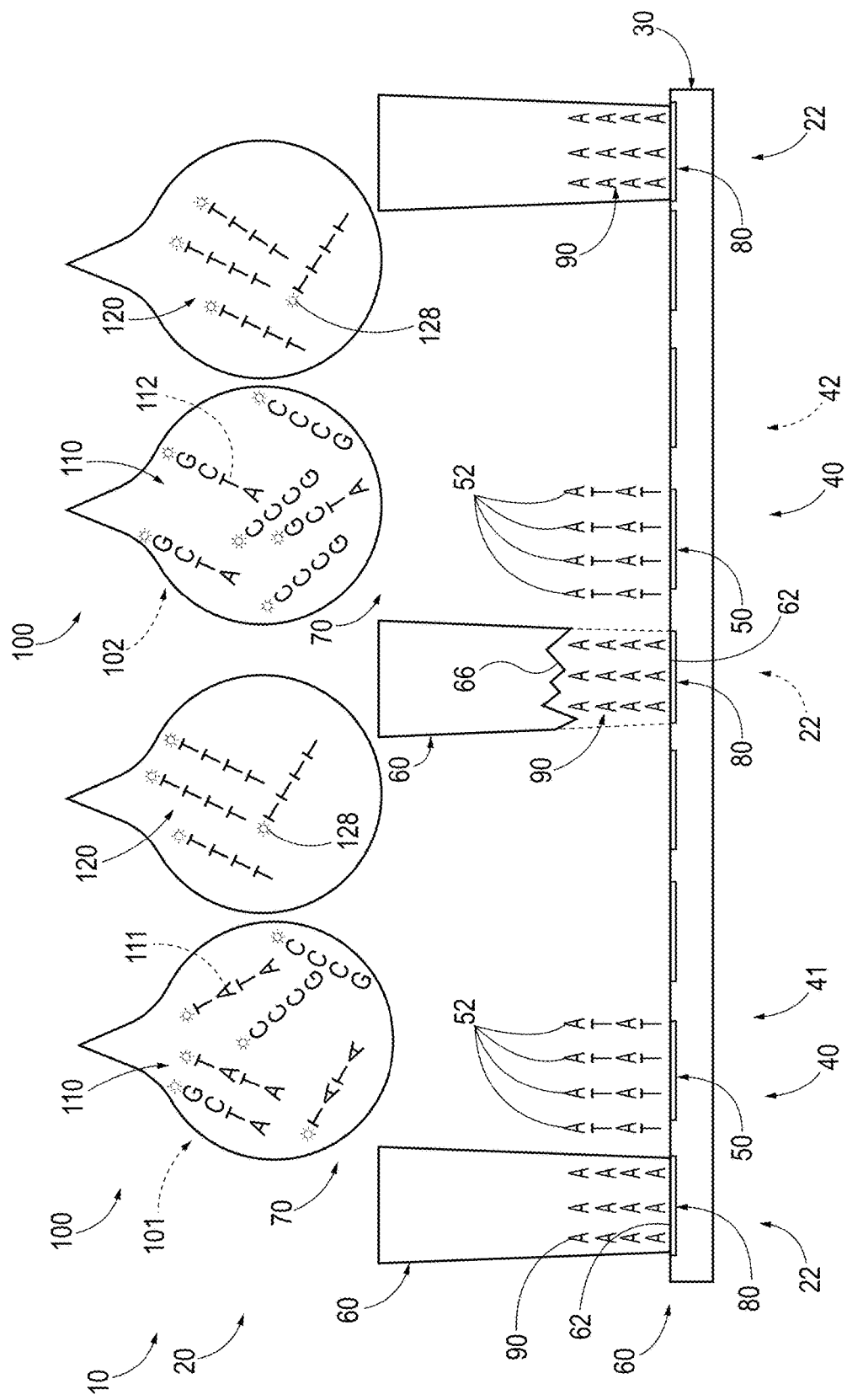
FIG. 6 is a schematic illustration of examples of the microarray chip of FIG. 1 taken along line A-A of FIG. 1 and prior to introduction of a sample solution.
Figure 7:
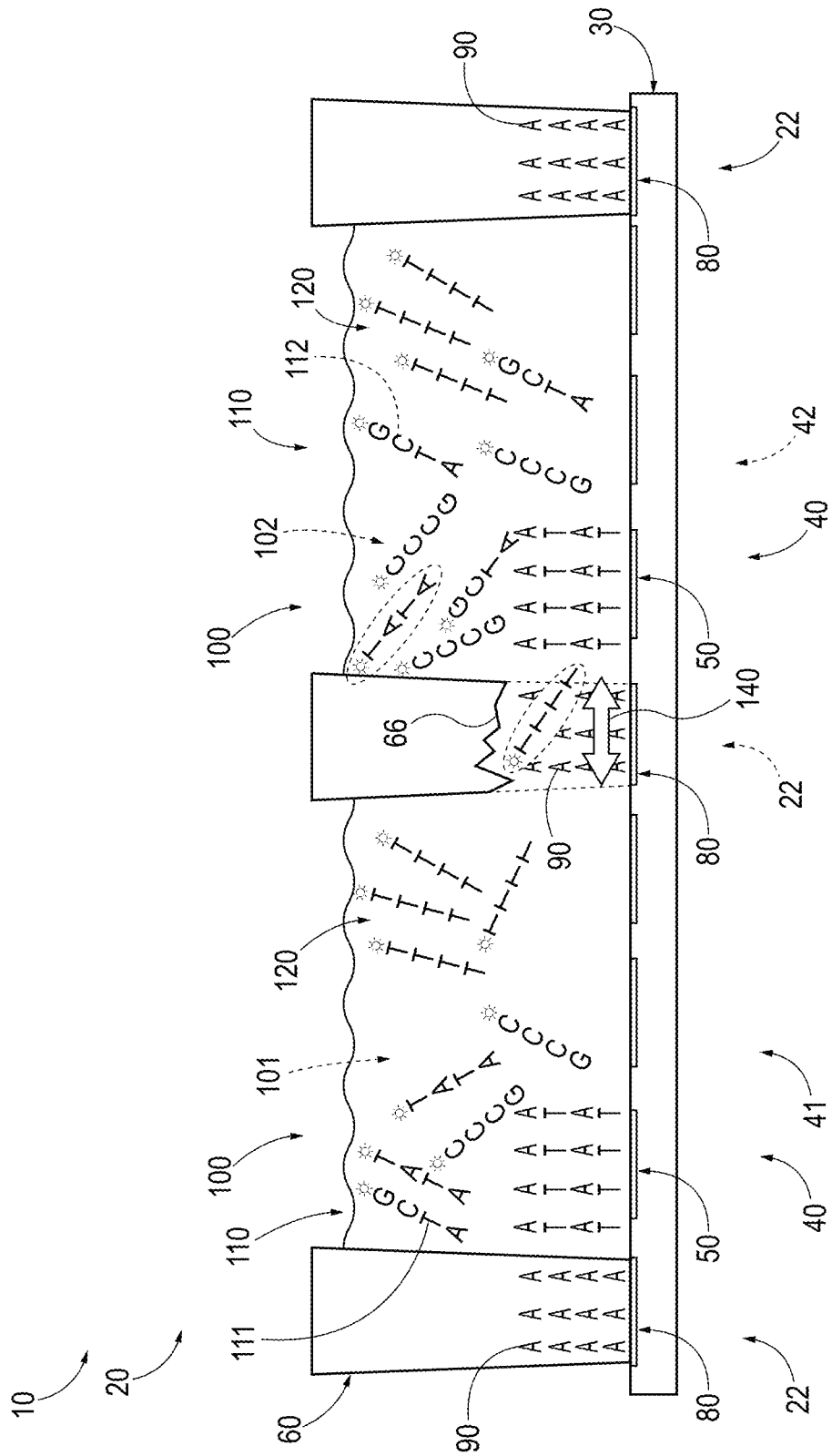
FIG. 7 is a schematic illustration of the microarray chip of FIG. 6 subsequent to introduction of the sample solution.

During operative use of chips 20, and as illustrated in FIG. 1, by the transition from the configuration that is illustrated in FIG. 2 to the configuration that is illustrated in FIG. 3, and/or by the transition from the configuration that is illustrated in FIG. 6 to the configuration that is illustrated in FIG. 7, a sample solution 100 may be positioned within one or more fluid-receiving wells 70 of chip 20. As also illustrated, sample solution 100 may include dissolved sample molecules (DSMs) 110, and chips 20 may be configured to identify, or to identify an oligonucleotide sequence of, DSMs 110. In some examples, sample solution 100 may be referred to herein as and/or may be an aqueous sample solution 100.

Figure 4:
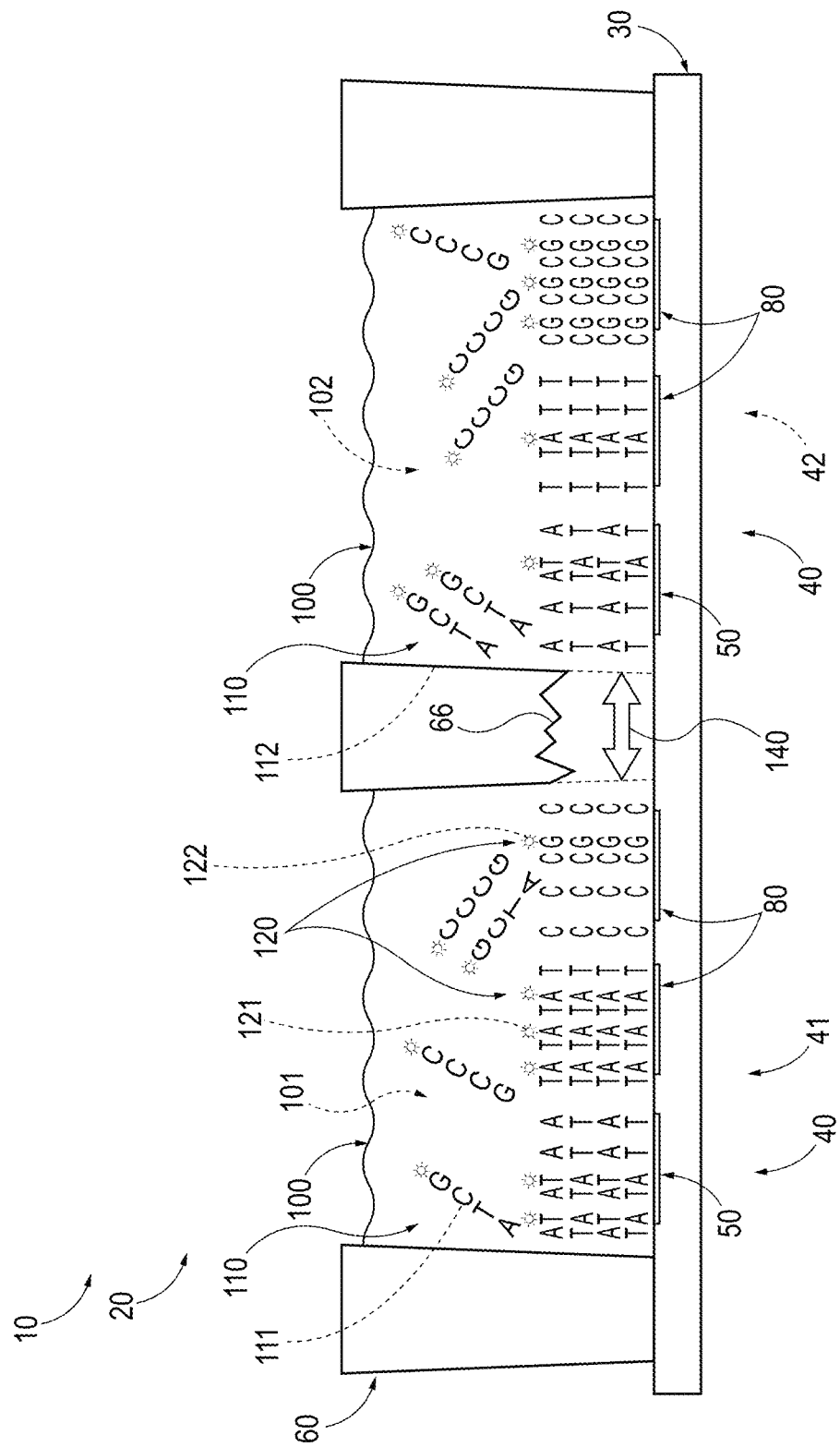
FIG. 4 is a schematic illustration of the microarray chip of FIG. 3 subsequent to a threshold hybridization time.
Figure 5:
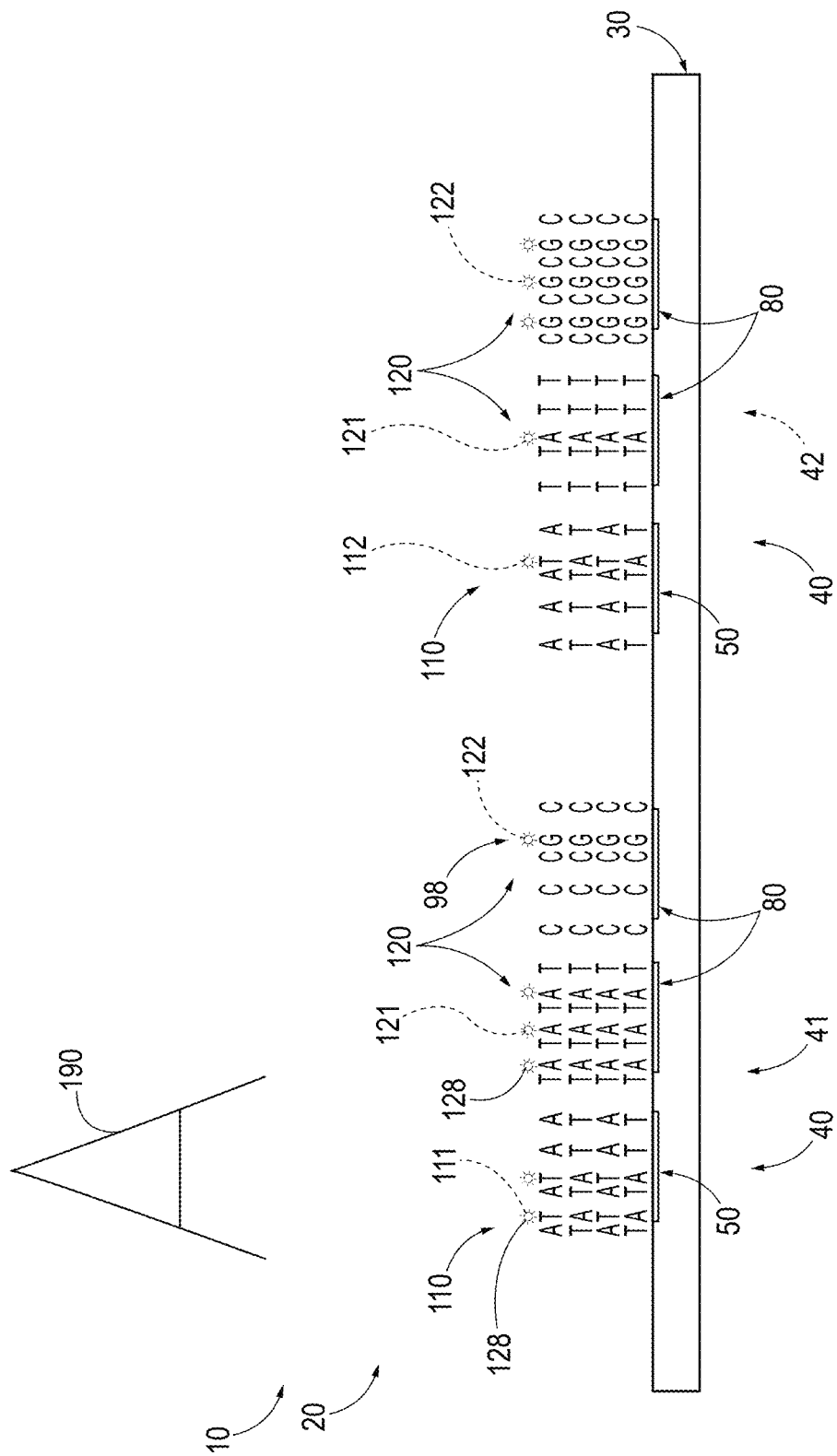
FIG. 5 is a schematic illustration of the microarray chip of FIG. 4 subsequent to draining the sample solution and removal of a perimeter sealing structure.
Figure 8:
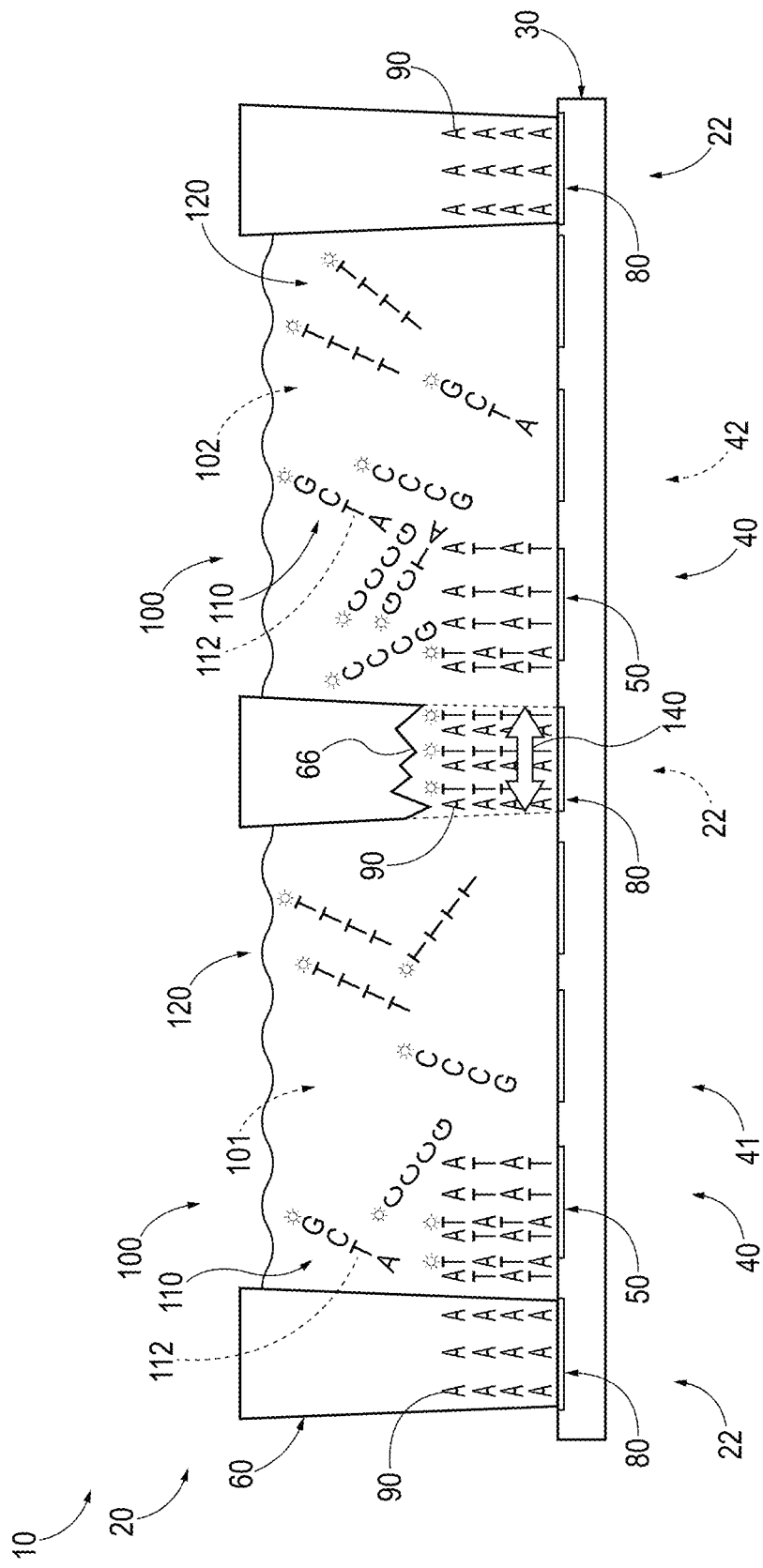
FIG. 8 is a schematic illustration of the microarray chip of FIG. 7 subsequent to a threshold hybridization time.
Figure 9:
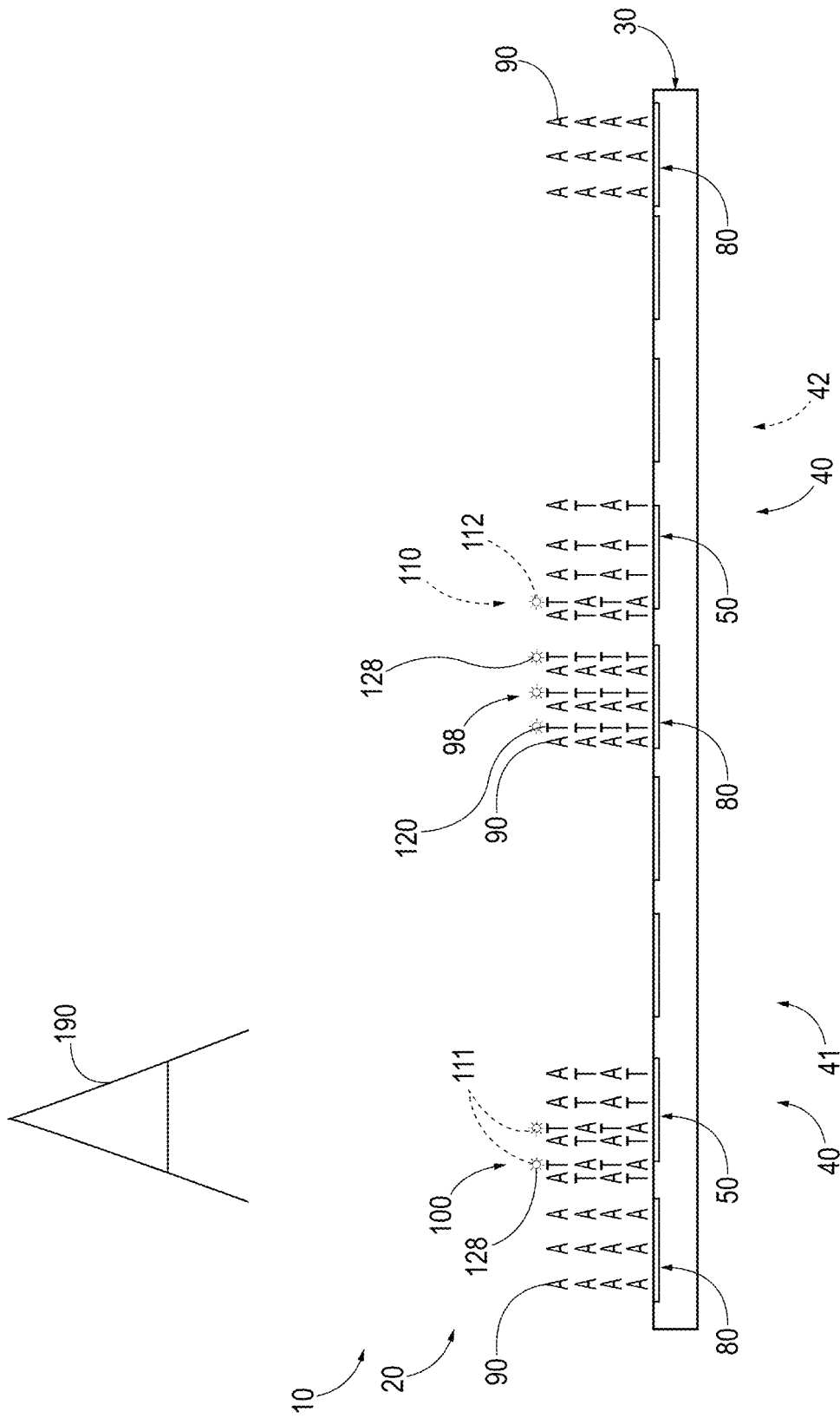
FIG. 9 is a schematic illustration of the microarray chip of FIG. 8 subsequent to draining the sample solution and removal of a perimeter sealing structure.

More specifically, DSMs 110 may move, migrate, and/or diffuse, within fluid-receiving wells 70, such that DSMs having dissolved sample oligonucleotide sequences that are complementary to the predetermined anchored test oligonucleotide sequence of ATMs 52 within a given test feature 50 hybridize with the ATMs of the given test feature, as illustrated in FIGS. 4 and 8. In the examples of FIGS. 4 and 8, DSMs with the oligonucleotide sequence TATA have hybridized with ATMs with the predetermined anchored test oligonucleotide sequence ATAT. Subsequently, and as illustrated by the transition from the configuration that is illustrated in FIG. 4 to the configuration that is illustrated in FIG. 5 and/or by the transition from the configuration that is illustrated in FIG. 8 to the configuration that is illustrated in FIG. 9, sample solution 100 may be drained from given subarray 41, perimeter sealing structure 60 may be removed, microarray chip 20 may be washed, and/or the microarray chip may be dried.

Then, an imaging device 190 may be utilized to detect the hybridization, thereby facilitating identification of the dissolved sample oligonucleotide sequence of DSMs 110. This may be accomplished in any suitable manner. As an example, DSMs 110 may include an attached fluorophore 128, and imaging device 190 may detect fluorescence from the attached fluorophore. Examples of imaging device 190 include a microscope, a fluorescence microscope, a camera, a video camera, a fluorescent charge coupled device camera, and/or a fluorescent scanner.

As discussed, perimeter sealing structure 60 is configured to fluidically isolate each subarray 40 from all other subarrays of chip 20. However, in practice, leaks 140 between adjacent subarrays 40 sometimes may occur. As an example, leaks 140 may be caused by and/or the result of damage 66 to perimeter sealing structure 60, such as is illustrated in solid lines for the central perimeter sealing structure 60. As another example, leaks 140 may be caused by and/or the result of formation of an imperfect fluid seal 62 between the perimeter sealing structure and substrate 30, such as may be illustrated in dashed lines for the central perimeter sealing structure 60. As another example, leaks 140 may be caused by and/or the result of contamination of one sample solution 100 with another sample solution 100, such as may be caused by cross-contamination when sample solutions 100 are positioned within corresponding subarrays 40. As another example, leaks 140 may be caused by and/or the result of any other mechanism via which a portion of a given sample solution 100 is positioned within a microarray 40 that differs from a target and/or desired microarray for the given sample solution. Leaks 140 may include leaks from a given subarray 41 to and/or into an interstitial void space 24 between adjacent subarrays 40, as illustrated in FIG. 1. Additionally or alternatively, leaks 140 also may include leaks from the given subarray to an adjacent subarray, as illustrated in FIGS. 1, 3-4, and 7-8.

As discussed, conventional microarray chips generally are not configured to detect, or to directly detect, leaks from and/or into corresponding subarrays. Instead, statistical analyses often are utilized to infer the presence of a leak; however, such analyses generally cannot be utilized to definitively identify the presence and/or source of a leak and instead simply indicate that a given dataset may be questionable and/or that a given experiment should be repeated.

In contrast, microarray chips 20, according to the present disclosure, include leak detection regions 80 and are configured for direct detection of leaks 140 and/or of cross-contamination produced and/or generated by leaks 140. To facilitate this detection, microarray chips 20 may be utilized with dissolved leak detection molecules (DLDMs) 120 and, in such configurations, may be referred to herein as a kit 10 of components configured to facilitate detection of a leak, or a fluid leak. DLDMs 120 are configured to be dissolved within sample solution 100 for given subarray 41 and define a predetermined dissolved leak detection oligonucleotide sequence that is complementary to the predetermined anchored leak detection oligonucleotide sequence of ALDMs 90. As such, DLDMs 120 may be configured to hybridize with ALDMs 90 when fluid that includes DLDMs 120 contacts ALDMs 90. Similar to DSMs 110, DLDMs 120 may include attached fluorophores 127, and this hybridization may be detected in a manner that is similar to detection of hybridization between DSMs 110 and ATMs 52, which is discussed herein. In addition, and as discussed in more detail herein, microarray chips 20 may be configured such that DLDMs 120 only contact ALDMs 90, or only contact specific ALDMs 90, when leak 140 exists. As an example, at least one leak detection region 80 may be external given subarray 41. Thus, detection of the hybridization, or of hybridization at a specific location, may be utilized to indicate the presence of leak 140.

In some examples, and as illustrated in FIGS. 1-5, microarray chips 20 may be configured to detect leak 140 between adjacent subarrays 40 of the microarray chips. As an example, given subarray 41 also may be referred to herein as and/or may be a first subarray 41, and microarray chips 20 may include a second subarray 42 that is adjacent to the first subarray. In such examples, leak detection region 80 may be positioned within second subarray 42, and perimeter sealing structure 60 may be configured to fluidically isolate the first subarray from the second subarray. However, leak 140 may permit dissolved leak detection molecules 120 that originally are positioned within first subarray 41, as illustrated in FIG. 2, to flow, diffuse, and/or migrate into second subarray 42, as illustrated in FIGS. 3-5, thereby permitting detection of the leak detection molecules within the second subarray an indicating leak 140 from the first subarray to the second subarray.

In practice, microarray chips 20 may be configured to detect leak 140 in both directions. Stated differently, the microarray chip may be configured to detect leak 140 both from first subarray 41 into second subarray 42 and from second subarray 42 into first subarray 41. With this in mind, and as illustrated, leak detection region 80 that is positioned within second subarray 42 may be referred to herein as a second leak detection region 82, and microarray chip 20 also may include a first leak detection region 81 that is positioned within first microarray 41.

In such a configuration, both leak detection regions 80 (i.e., first leak detection region 81 and second leak detection region 82) may include ALDMs 90 in the form of first ALDMs 91 and second ALDMs 92, as indicated in FIGS. 1-2. First ALDMs 91 and second ALDMs 92, which also may be referred to herein as groupings of first ALDMs 91 and groupings of second ALDMs 92 and/or as leak detection features of first ALDMs 91 and leak detection features of second ALDMs 92, may be spaced-apart from one another, may be adjacent to one another, and/or may be positioned within different areas of leak detection regions 80. First ALDMs 91 may define a first predetermined anchored leak detection oligonucleotide sequence, and second ALDMs 92 may define a second predetermined anchored leak detection oligonucleotide sequence that differs from the first predetermined anchored leak detection oligonucleotide sequence.

Also in such a configuration, and as illustrated in FIGS. 1-2, a first sample solution 101 may be provided to first subarray 41 and a second sample solution 102, which differs from the first sample solution, may be provided to second subarray 42. In some examples, first sample solution 101 may include first DSMs 111, and second sample solution 102 may include second DSMs 112 that differ from first DSMs 111. However, this is not required, and it is within the scope of the present disclosure that first sample solution 101 and second sample solution 102 may include the same DSMs 110.

However, in the example illustrated in FIGS. 2-5, DLDMs 120 provided to first subarray 41 differ from DLDMs 120 provided to second subarray 42. As an example, DLDMs 120 in the form of first DLDMs 121 may be provided to first subarray 41, and DLDMs 120 in the form of second DLDMs 122 may be provided to second subarray 42. First DLDMs 121 may define a first predetermined dissolved leak detection oligonucleotide sequence, which may be complementary to the first predetermined anchored leak detection oligonucleotide sequence of first ALDMs 91. Second DLDMs 122 may define a second predetermined dissolved leak detection oligonucleotide sequence, which may be complementary to the second predetermined anchored leak detection oligonucleotide sequence of second ALDMs 92 and/or may differ from the first predetermined dissolved leak detection oligonucleotide sequence of DLDMs 121.

As discussed in more detail herein, the above-described configuration may provide a number of distinct benefits over conventional microarray chips. As an example, and independent of the presence of leak 140, hybridization between first DLDMs 121 and first ALDMs 91 within first leak detection region 81 of first subarray 41 is expected to occur. Similarly, and independent of the presence of the leak, hybridization between second DLDMs 122 and second ALDMs 92 within second leak detection region 82 of second subarray 42 also is expected to occur. As such, detection of these hybridizations may be utilized as "control" experiments to verify the presence of first DLDMs 121 within first sample solution 101, to verify the presence of second DLDMs 122 within second sample solution 102, and/or to verify integrity of the overall testing and hybridization methodology.

As another example, hybridization between first DLDMs 121 and first ALDMs 91 within second leak detection region 82 of second subarray 42 is only expected to occur via leak 140, as perhaps best illustrated in FIGS. 2-3. Similarly, hybridization between second DLDMs 122 and second ALDMs 92 within first leak detection region 81 of first subarray 41 only is expected to occur via leak 141, as also illustrated in FIGS. 2-3. As such, detection of these hybridizations may be utilized to determine, establish, verify, and/or indicate the presence of leak 140. Furthermore, the relative magnitude of these hybridizations, such as may be indicated by the relative intensity of fluorescence, may be utilized to indicate the magnitude of leak 140.

It is within the scope of the present disclosure that microarray chips 20 may be configured to detect leaks from and/or between any suitable number of subarrays. In some examples, microarray chips 20 may be configured, or only may be configured, to detect leaks from and/or between adjacent subarrays; however, this is not required. As used herein, the term "adjacent" when utilized to describe the spatial relationship between subarrays, may indicate that the subarrays share a wall and/or a corner of perimeter sealing structure 60. As an example, and with reference to FIG. 1, first subarray 41 may be referred to herein as being adjacent to 5 other subarrays 40, one above, one below, one to the right, one diagonally above and to the right, and one diagonally below and to the right. Similarly, second subarray 42 may be referred to herein as being adjacent to 8 other subarrays 40, as illustrated. It is also within the scope of the present disclosure that FIG. 1 only illustrates a region of microarray chip 20 and/or that each subarray 40 of FIG. 1 is adjacent to 8 other subarrays. Stated differently, FIG. 1 may illustrate a configuration in which a repeat unit for subarrays 40 includes 9 subarrays 40, as illustrated.

With this in mind, and with reference to FIG. 1, each subarray 40 may include a corresponding leak detection region 80, and each corresponding leak detection region 80 may include a number of distinct ALDM features 94. The number of distinct ALDM features may correspond to the number of adjacent subarrays. As an example, and when microarray chips 20 are configured to detect, or only to detect, leaks from and/or between adjacent subarrays, the number of distinct ALDM features may be one greater than the number of adjacent subarrays and/or may equal the number of subarrays in the repeat unit for subarrays. As a more specific example, and in the configuration that is illustrated in FIG. 1, the central subarray 40 has 8 adjacent subarrays 40, and each corresponding leak detection region 80 may include 9 distinct ALDM features. As another example, the number of distinct ALDM features may be expanded to corresponding to the number of subarrays 40 on the microarray chip and/or within a given region of the microarray chip. Such a configuration may permit and/or facilitate detection of leaks across greater distances and/or between non-adjacent subarrays, such as may be caused by cross-contamination of the subarrays when the sample solutions are positioned therein.

As illustrated, each ALDM feature of the number of distinct ALDM features 94 may be spaced-apart from each other ALDM feature of the number of distinct ALDM features. Additionally or alternatively, each ALDM feature may include corresponding ALDMs that define a corresponding predetermined anchored leak detection oligonucleotide sequence that differs from the predetermined anchored leak detection oligonucleotide sequence of each other ALDM feature. Stated differently, each ALDM feature may be configured to hybridize with different corresponding DLDMs 120 and/or with one unique corresponding DLDM 120. As such, and during operative use of microarray chips 20, different DLDMs 120, each of which may define a unique and/or corresponding predetermined dissolved leak detection oligonucleotide sequence that is complementary to only one ALDM feature 94, may be positioned within each subarray 40. As such, detection of hybridization between given DLDMs 120 and the corresponding ALDM feature within a subarray 40 other than the one to which the given DLDMs initially were provided may be indicative of a leak. In addition, a source subarray for the leak may be determined based upon knowledge of the subarray to which the given DLDMs initially were provided.

In some examples, and as illustrated in FIGS. 1 and 6-9, microarray chips 20 may be configured to detect leak 140 via detection of DLDMs 120 within a region of microarray chip 20 that is external to all subarrays 40, within contact region 64 between perimeter sealing structure 60 and substrate 30, and/or within unwetted region 22 of the microarray chip. Stated differently, and in such examples, leak detection region 80 may be positioned, or at least partially positioned, within the region of the microarray chip that is external all subarrays 40, within the contact region between the perimeter sealing structure and the substrate, and/or within the unwetted region of the microarray chip.

In such a configuration, and as illustrated in FIG. 6, sample solutions 100 that include the same DLDMs 120 may be provided to all subarrays 40 and/or to fluid-receiving wells 70 thereof. As illustrated in solid lines on the leftmost and rightmost sides of FIG. 7 and in dashed lines in the middle of FIG. 7, the presence of perimeter sealing structure 60 may preclude contact between DLDMs 120 and ALDMs 90 within regions of microarray chip 20 where leak 140 does not exist. However, in regions of the microarray chip where there is damage 66 to the perimeter sealing structure and/or where leak 140 is present, DLDMs 120 may come into contact and hybridize with ALDMs 90, as illustrated in FIG. 8. This hybridization may be detected, as illustrated in FIG. 9, thereby permitting and/or facilitating identification of leak 140. More specifically, the presence of leak 140 will cause detection of hybridization, such as via detection of fluorescence, in the region of the microarray chip where the leak occurred, thereby providing a visible indication of both the presence of the leak and the leakage pathway for the leak.

As discussed herein, ATMs 52, ALDMs 90, DSMs 110, and DLDMs 120 all include and/or define corresponding oligonucleotide sequences. For simplicity, and in the illustrative examples of FIGS. 2-9, ATMs 52, ALDMs 90, DSMs 110, and DLDMs 120 each include four nucleotides. However, it is within the scope of the present disclosure that these molecules may include any suitable number of nucleotides, examples of which include at least 2, at least 4, at least 6, at least 8, at least 10, at least 15, at least 20, at least 25, at least 30, at least 40, at least 50, at most 200, at most 150, at most 100, at most 75, at most 50, at most 40, at most 30, and/or at most 20 nucleotides.

Hybridization alone may be challenging to directly detect, measure, and/or determine. Thus, and as discussed, DSMs 110 and DLDMs 120 may include attached fluorophores 128, which may permit and/or facilitate indirect detection of hybridization via detection of fluorescence from the attached fluorophores within regions of microarray chip where hybridization occurs, as is discussed herein.

Substrate 30 may include any suitable structure that may be adapted and/or configured to have subarrays 40 formed thereon, to have leak detection regions 80 formed thereon, and/or that may be configured to form the fluid seal with perimeter sealing structure 60. Examples of substrate 30 include a planar substrate, an at least substantially planar substrate, an optically transparent substrate, an at least substantially optically transparent substrate, a glass substrate, and/or a polymeric substrate.

Perimeter sealing structure 60 may include any suitable structure that may be adapted and/or configured to form the fluid seal with substrate 30, to at least partially define fluid-receiving wells 70, and/or to fluidically isolate each subarray 40 from all other subarrays 40. Examples of perimeter sealing structure 60 include a resilient sealing structure, an elastomeric sealing structure, a gasket, and/or an O-ring. In some examples, a single, monolithic, and/or unitary perimeter sealing structure 60 may fluidically isolate all subarrays 40 and/or may at least partially define all fluid-receiving wells 70 of microarray chip 20. Additionally or alternatively, each subarray 40 may be associated with a corresponding perimeter sealing structure 60, which may be spaced-apart from other, of from all other, sealing structures 60. In such a configuration, and as illustrated in FIG. 1, microarray chips 20 may define interstitial void space 24 between adjacent subarrays 40.

Figure 10:
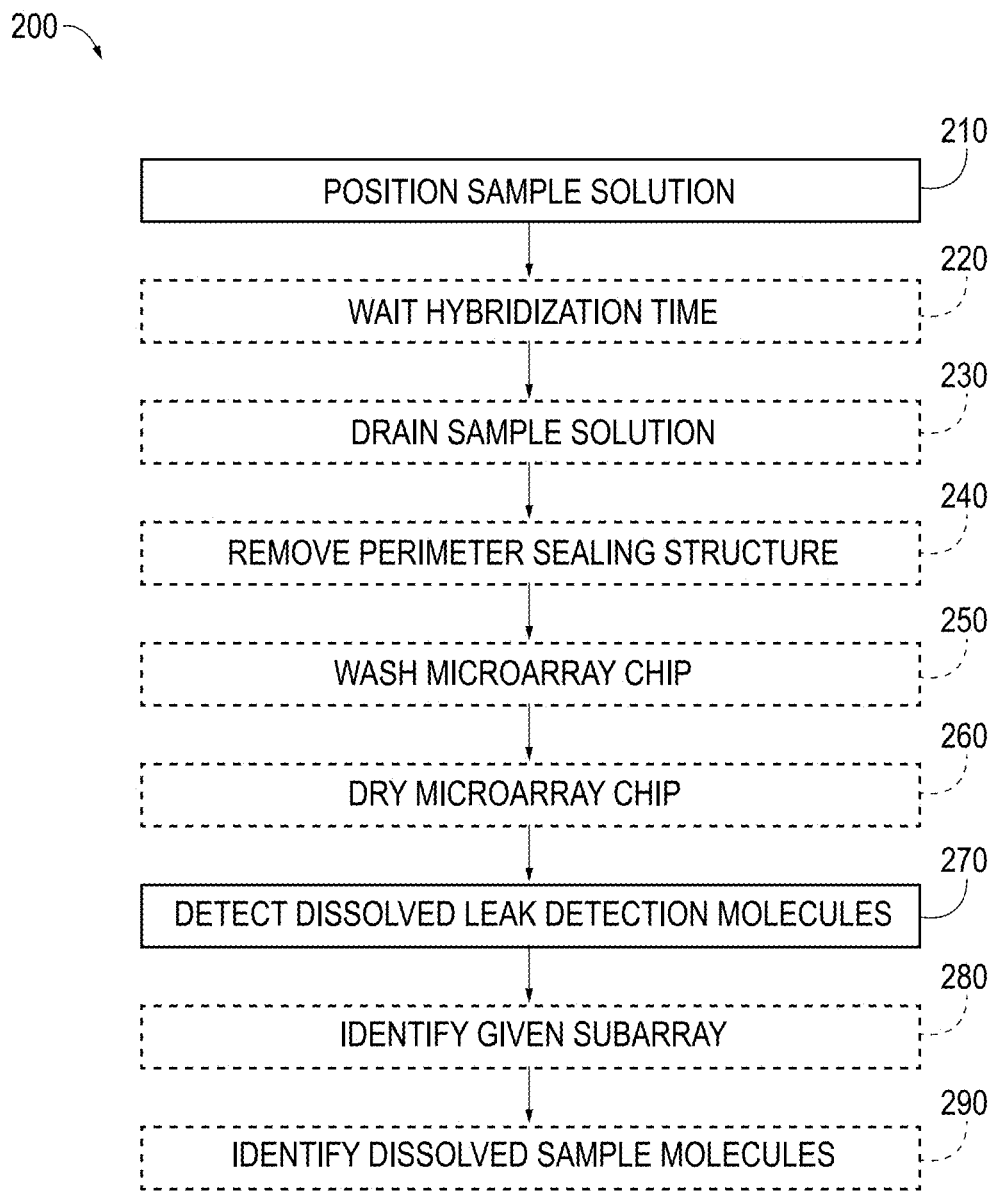
FIG. 10 is a flowchart depicting examples of methods of detecting a leak within a microarray chip, according to the present disclosure.

FIG. 10 is a flowchart depicting examples of methods 200 of detecting a leak from a given subarray of a plurality of subarrays that are formed on a substrate and together define a microarray chip, according to the present disclosure. Methods 200 include positioning a sample solution at 210 and may include waiting a hybridization time at 220, draining the sample solution at 230, removing a perimeter sealing structure at 240, washing the microarray chip at 250, and/or drying the microarray chip at 260. Methods 200 also include detecting dissolved leak detection molecules at 270 and may include identifying the given subarray at 280 and/or identifying dissolved sample molecules at 290. Examples of the leak are disclosed herein with reference to leak 140. Examples of the microarray chip and/or components thereof are disclosed herein with reference to microarray chips 20.

Positioning the sample solution at 210 may include positioning the sample solution within the given subarray. The sample solution includes dissolved samples molecules (DSMs) that define a dissolved sample oligonucleotide sequence. The sample solution also includes dissolved leak detection molecules (DLDMs) that define a predetermined dissolved leak detection oligonucleotide sequence.

The positioning at 210 may be performed in any suitable manner. As an example, and while not required, the microarray chip may define a plurality of open-top fluid-receiving wells, examples of which are disclosed herein with reference to fluid-receiving wells 70. In such an example, the positioning at 210 may include positioning the sample solution into a corresponding open-topped fluid-receiving well, such as via a corresponding open top thereof.

As discussed in more detail herein, each subarray includes a perimeter sealing structure configured to form a fluid seal with the substrate, to at least partially define the open-top fluid-receiving wells, and/or to fluidically isolate the subarrays from one another. As also discussed in more detail herein, each subarray includes a plurality of test features each of which includes anchored test molecules (ATMs). The ATMs are anchored to the substrate and define a predetermined anchored test oligonucleotide sequence.

As also discussed in more detail herein, the microarray chip includes a leak detection region that includes anchored leak detection molecules (ALDMs). The ALDMs are attached to the substrate and define a predetermined anchored leak detection oligonucleotide sequence that is complementary to the dissolved leak detection oligonucleotide sequence of the DLDMs.

Waiting the hybridization time at 220 may include waiting any suitable hybridization time that is subsequent to the positioning at 210 and prior to the detecting at 270. This may include waiting to permit the DLDMs to diffuse to the region of the microarray chip that is external the given subarray and//or to diffuse to and/or to hybridize with ALDMs. Examples of the threshold diffusion time include at least 30 minutes (min), at least 45 min, at least 1 hour (hr.), at least 1.5 hr., at least 2 hr., at least 3 hr., at least 4 hr., at least 5 hr., at least 6 hr., at least 7 hr., at least 8 hr., at least 9 hr., at least 10 hr., at least 11 hr., at least 12 hr., at least 13 hr., at least 14 hr., at least 15 hr., at least 16 hr., at least 17 hr., at least 18 hr., at least 19 hr., at least 20 hr., at least 22 hr., at least 24 hr., at most 100 hr., at most 90 hr., at most 80 hr., at most 70 hr., at most 60 hr., at most 50 hr., at most hr., at most 30 hr., at most 20 hr., at most 10 hr., at most 8 hr., at most 6 hr., at most 4 hr., and/or at most 2 hr.

Draining the sample solution at 230 may include draining the sample solution from the given subarray and may be performed subsequent to the waiting at 220 and/or prior to the detecting at 270. This may include draining the sample solution from the given subarray to permit and/or to facilitate the removing at 240, the washing at 250, the drying at 260, and/or the detecting at 270. Additionally or alternatively, the draining at 230 may include draining the sample solution to decrease a potential for cross-contamination among the plurality of subarrays.

Removing the perimeter sealing structure at 240 may include removing the perimeter sealing structure from the microarray chip and/or separating the perimeter sealing structure from the substrate and may be performed subsequent to the waiting at 220, subsequent to the draining at 230, subsequent to the washing at 250, prior to the washing at 250, prior to the drying at 260, and/or prior to the detecting at 270. This may include removing the perimeter sealing structure to permit and/or to facilitate the washing at 250, the drying at 260, and/or the detecting at 270.

Washing the microarray chip at 250 may include washing the microarray chip, or at least a region of the microarray chip, utilizing one or more solvents and may be performed subsequent to the waiting at 220, subsequent to the draining at 230, subsequent to the removing at 240, prior to the removing at 240, and/or prior to the drying at 260. This may include washing to separate unhybridized DSMs and/or unhybridized DLDMs from the substrate. Stated differently, the washing at 250 may be utilized to improve a signal-to-noise ratio of the detecting at 270, such as via removing fluorophores that are associated with unhybridized molecules from the microarray chip.

Drying the microarray chip at 260 may include removing liquid and/or moisture from the microarray chip and may be performed subsequent to the waiting at 220, subsequent to the draining at 230, subsequent to the removing at 240, subsequent to the washing at 250, and/or prior to the detecting at 270. This may include drying the microarray chip to decrease mobility of DSMs that are hybridized with corresponding ATMs, to decrease mobility of DLDMs that are hybridized with corresponding ALDMs, and/or to increase an overall stability of the microarray chip prior to the detecting at 270.

Detecting DLDMs at 270 may include detecting the DLDMs within a region of the microarray chip that is external to and/or spaced-apart from the given subarray. Stated differently, the presence of the leak may permit and/or facilitate motion of the DLDMs out of the given subarray and/or to the region of the microarray chip that is external to the given subarray, and the detecting at 270 may include detecting that the DLDMs are external to the given subarray. The detecting at 270 may be accomplished in any suitable manner. As an example, and as discussed, the detecting at 270 may include detecting hybridization between the ALDMs and the DLDMs. As a more specific example, and as also discussed, the DLDMs may include attached fluorophores, and the detecting at 270 may include detecting fluorescence from the attached fluorophores, such as via utilizing an imaging device and/or a fluorescence microscope.

Identifying the given subarray at 280 may include identifying a spatial location of the given subarray, on the microarray chip, based, at least in part, on the detecting at 270. As an example, and as discussed in more detail herein, different DLDMs may be positioned within each subarray of the plurality of subarrays, and the identifying at 280 may include identifying the given subarray based, at least in part, on an identity of the DLDMs and/or on a location, within the microarray chip, at which hybridization occurs. As another example, and as also discussed in more detail herein, the identifying at 280 may include identifying regions of the substrate that only will exhibit hybridization with the DLDMs when the leak occurs.

Identifying the DSMs at 290 may include identifying the DSMs in any suitable manner and/or based upon any suitable criteria. As an example, and as discussed in more detail herein, the DSMs may have a dissolved sample oligonucleotide sequence that hybridizes with certain and/or specific ATMs of the microarray chip. As such, the detecting at 270 further may include detecting hybridization between the DSMs and the certain and/or specific ATMs, and the identifying at 290 may include identifying the DSMs based, at least in part, on the predetermined anchored test oligonucleotide sequence of the ATMs with which the DSMs hybridize.

In a specific example, and as illustrated in FIGS. 1-5 and discussed in more detail herein with reference thereto, the given subarray may include and/or be first subarray 41, the microarray chip also may include second subarray 42, and the leak detection region may be positioned external first subarray 41 and/or within second subarray 42. In such a configuration, the positioning at 210 may include positioning first sample solution 101, which includes first DSMs 111 and first DLDMs 121, within first subarray 41 and also positioning second sample solution 102, which includes second DSMs 112 and second DLDMs 122, within second subarray 42. In such a configuration, the detecting at 270 may include detecting a first leak from first subarray 41 to second subarray 42 via detection of hybridization between first DLDMs 121 and first ALDMs 91 of second subarray 42 and/or detecting a second leak from second subarray 42 to first subarray 41 via detection of hybridization between second DLDMs 122 and second ALDMs 92 of first subarray 41.

Also in such a configuration, and as discussed, a control experiment simultaneously may be performed. In particular, the detecting at 270 may include detecting hybridization between first DLDMs 121 and first ALDMs 91 of first subarray 41 and confirming presence of first DLDMs 121 within first sample solution 101 responsive thereto. Additionally or alternatively, the detecting at 270 may include detecting hybridization between second DLDMs 122 and second ALDMs 92 of second subarray 42 and confirming presence of second DLDMs 122 within second sample solution 102 responsive thereto.

As also discussed in more detail herein with reference to FIGS. 1-5, methods 200 may be expanded to detect leaks to and/or from any suitable number of adjacent subarrays within the microarray chip and/or among any suitable subset, or even all, subarrays within the microarray chip. In such a configuration, the positioning at 210 may include positioning, within each subarray, a corresponding sample solution of a plurality of sample solutions. Each corresponding sample solution includes corresponding DSMs 110 and corresponding DLDMs 120. Corresponding DLDMs 120 define a corresponding predetermined dissolved leak detection oligonucleotide sequence that is complementary to the corresponding predetermined anchored leak detection oligonucleotide sequence of only one ALDM feature 94 of the number of distinct ALDM features and differs from a corresponding DLDMs of each other sample solution of the plurality of sample solutions. As such, detection, during the detecting at 270, of hybridization between corresponding DLDMs 120 and any ALDM feature 94 that is external the subarray within which the corresponding DLDMs 120 were positioned during the positioning at 210 is indicative of a leak.

In another specific example, and as illustrated in FIGS. 1 and 5-9 and discussed in more detail herein with reference thereto, leak detection region 80 may be external all subarrays 40, maybe positioned within contact region 64 between the perimeter sealing structure and the substrate, may be positioned in unwetted region 22 of the microarray chip, and/or may include a single ALDM 90 with a single attached leak detection oligonucleotide sequence for an entirety of microarray chip 20. In such a configuration, the positioning at 210 may include positioning, within each subarray 40, a corresponding sample solution 100 of a plurality of sample solutions. Each corresponding sample solution may include corresponding DSMs 110 and the same DLDMs 120. Stated differently, it is within the scope of the present disclosure that sample solutions 100 will include different DSMs 110; however, the same DLDMs 120 will be utilized in each sample solution 100. In such a configuration, the detecting at 270 may include detecting hybridization between ALDMs 90 and DLDMs 120 external to all subarrays 40, within contact region 64, and/or within unwetted region 22. Such a configuration may provide a visual indication of a leakage pathway of the leak, such as via detection of fluorescence from the leakage pathway.

ATMs 52, ALDMs 90, DSMs 110, and DLDMs 120 have been described as including and/or defining corresponding oligonucleotide sequences. It is within the scope of the present disclosure that the methods, kits, and microarray chips, which are disclosed herein, may include and/or may be utilized with additional and/or other moieties, which are not necessarily required to include nucleotides and/or to define corresponding oligonucleotide sequences. Examples of such other moieties include locked nucleic acids (LNA), peptide nucleic acids (PNA), and/or proteins.

Kits 10, microarray chips 20, and/or methods 200 generally have been described in the context of microarray chips 20 that include one or two-dimensional arrangements of subarrays 40 on a substrate 30. It is within the scope of the present disclosure that the disclosed leak detection methodologies may be utilized in other configurations, an example of which includes a flow cell in which different reactions take place in spaced-apart and/or distinct flow channels.

In the present disclosure, several of the illustrative, non-exclusive examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, "at least substantially," when modifying a degree or relationship, may include not only the recited "substantial" degree or relationship, but also the full extent of the recited degree or relationship. A substantial amount of a recited degree or relationship may include at least 75% of the recited degree or relationship. For example, an object that is at least substantially formed from a material includes objects for which at least 75% of the objects are formed from the material and also includes objects that are completely formed from the material. As another example, a first length that is at least substantially as long as a second length includes first lengths that are within 75% of the second length and also includes first lengths that are as long as the second length.

Illustrative, non-exclusive examples of kits, microarray chips, and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. A method of detecting a leak from a given subarray of a plurality of subarrays that are formed on a substrate and together define a microarray chip, the method comprising:

positioning, within the given subarray, a sample solution that includes:

(i) dissolved sample molecules (DSMs) that define a dissolved sample oligonucleotide sequence; and (ii) dissolved leak detection molecules (DLDMs) that define a predetermined dissolved leak detection oligonucleotide sequence; and detecting the DLDMs within a region of the microarray chip that is external the given subarray.

A2. The method of paragraph A1, wherein each subarray of the plurality of subarrays includes:

(i) a perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and (ii) a plurality of test features, wherein each test feature of the plurality of test features includes anchored test molecules (ATMs), which are anchored to the substrate and define a predetermined anchored test oligonucleotide sequence; and wherein the microarray chip further includes a leak detection region, wherein the leak detection region includes anchored leak detection molecules (ALDMs), which are attached to the substrate and define a predetermined anchored leak detection oligonucleotide sequence that is complementary to the dissolved leak detection oligonucleotide sequence; and further wherein the detecting the DLDMs includes detecting hybridization between the ALDMs and the DLDMs.

A3. The method of paragraph A2, wherein the predetermined anchored test oligonucleotide sequence of each test feature differs from the predetermined anchor test sequence of at least one of:
(i) at least one other test feature of the plurality of test features;
(ii) a majority of the other test features of the plurality of test features; and
(iii) all other test features of the plurality of test features.

A4. The method of any of paragraphs A2-A3, wherein the predetermined anchored leak detection oligonucleotide sequence of the leak detection region differs from the predetermined anchored test oligonucleotide sequence of every test feature of the plurality of test features.

A5. The method of any of paragraphs A2-A4, wherein:
(i) the given subarray is a first subarray;
(ii) the microarray chip further includes a second subarray, which is adjacent to the first subarray; and
(iii) the leak detection region is positioned within the second subarray.

A6. The method of paragraph A5, wherein the perimeter sealing structure is configured to fluidically isolate the first subarray from the second subarray.

A7. The method of any of paragraphs A5-A6, wherein the leak detection region is a second leak detection region, and further wherein the microarray chip includes a first leak detection region that is positioned within the first subarray.

A8. The method of paragraph A7, wherein the ALDMs are first ALDMs, wherein the predetermined anchored leak detection oligonucleotide sequence is a first predetermined anchored leak detection oligonucleotide sequence, wherein the first leak detection region and the second leak detection region both include the first ALDMs, and further wherein the first leak detection region and the second leak detection region both include second ALDMs, which are spaced-apart from the first ALDMs and define a second predetermined anchored leak detection oligonucleotide sequence that differs from the first predetermined anchored leak detection oligonucleotide sequence.

A9. The method of paragraph A8, wherein the sample solution is a first sample solution, wherein the DSMs are first DSMs that define a first dissolved sample oligonucleotide sequence, wherein the DLDMs are first DLDMs that define a first predetermined dissolved leak detection oligonucleotide sequence, and further wherein the positioning includes positioning, within the second subarray, a second sample solution that includes:
(i) second DSMs that define a second dissolved sample oligonucleotide sequence; and
(ii) second DLDMs that define a predetermined second dissolved leak detection oligonucleotide sequence that is complementary to the second predetermined anchored leak detection oligonucleotide sequence.

A10. The method of paragraph A9, wherein the detecting includes detecting a first leak from the first subarray to the second subarray, and further wherein the method includes detecting a second leak from the second subarray to the first subarray via detecting hybridization between the second DLDMs and the second ALDMs of the first subarray.

A11. The method of any of paragraphs A9-A10, wherein the method further includes at least one of:
(i) detecting hybridization between the first DLDMs and the first ALDMs of the first subarray and confirming presence of the first DLDMs within the first sample solution responsive thereto; and
(iii) detecting hybridization between the second DLDMs and the second ALDMs of the second subarray and confirming presence of the second DLDMs within the second sample solution responsive thereto.

A12. The method of any of paragraphs A2-A11, wherein each subarray includes a corresponding leak detection region, wherein a spatial arrangement of the plurality of subarrays defines a number of adjacent subarrays, and further wherein each corresponding leak detection region includes a number of distinct ALDM features that corresponds to the number of adjacent subarrays, wherein each ALDM feature of the number of distinct ALDM features:
(i) is spaced apart from each other ALDM feature of the number of distinct ALDM features; and
(ii) includes corresponding ALDMs that define a corresponding predetermined anchored leak detection oligonucleotide sequence that differs from the predetermined anchored leak detection oligonucleotide sequence of each other ALDM feature.

A13. The method of paragraph A12, wherein the positioning includes positioning, within each subarray, a corresponding sample solution of a plurality of sample solutions, wherein the corresponding sample solution includes:
(i) corresponding DSMs; and
(ii) corresponding DLDMs that define a corresponding predetermined dissolved leak detection oligonucleotide sequence that is complementary to the corresponding predetermined anchored leak detection oligonucleotide sequence of only one ALDM feature of the number of distinct ALDM features and differs from a corresponding DLDMs of each other sample solution of the plurality of sample solutions.

A14. The method of paragraph A13, wherein the method further includes identifying the given subarray based, at least in part, on which corresponding DLDMs is detected during the detecting and within which subarray of the plurality of subarrays the corresponding DLDMs is positioned during the positioning.

A15. The method of any of paragraphs A1-A4, wherein at least one of the region of the microarray chip that is external the given subarray and a/the leak detection region is at least one of:
(i) external to all subarrays of the plurality of subarrays;
(ii) positioned within a contact region between a/the perimeter sealing structure and the substrate; and
(iii) positioned within an unwetted region of the microarray chip.

A16. The method of paragraph A15, wherein the positioning includes positioning, within each subarray, a corresponding sample solution of a plurality of sample solutions, wherein each corresponding sample solution includes:
(i) corresponding DSMs; and
(ii) the DLDMs, or the same DLDMs.

A17. The method of any of paragraphs A15-A16, wherein the detecting the DLDMs includes detecting hybridization between the ALDMs and the DLDMs at least one of:
(i) external to all subarrays of the plurality of subarrays;

(ii) within the contact region between the perimeter sealing structure and the substrate; and (iii) within the unwetted region of the microarray chip.

A18. The method of any of paragraphs A1-A17, wherein the microarray chip defines a plurality of open-topped fluid-receiving wells, wherein each open-topped fluid-receiving well defines a corresponding open top, and further wherein the positioning the sample solution includes positioning via the corresponding open top of the given subarray.

A19. The method of any of paragraphs A1-A18, wherein the DLDMs include attached fluorophores, and further wherein the detecting the DLDMs includes detecting fluorescence of the attached fluorophores within the region of the microarray chip that is external the given subarray.

A20. The method of paragraph A19, wherein the detecting includes detecting utilizing a fluorescence microscope.

A21. The method of any of paragraphs A1-A20, wherein, subsequent to the positioning and prior to the detecting, the method further includes waiting at least a threshold hybridization time for the DLDMs to diffuse to and hybridize with ALDMs within the region of the microarray chip that is external the given subarray.

A22. The method of paragraph A21, wherein the threshold diffusion time includes at least one of:
(i) at least 30 minutes (min), at least 45 min, at least 1 hour (hr.), at least 1.5 hr., at least 2 hr., at least 3 hr., at least 4 hr., at least 5 hr., at least 6 hr., at least 7 hr., at least 8 hr., at least 9 hr., at least 10 hr., at least 11 hr., at least 12 hr., at least 13 hr., at least 14 hr., at least 15 hr., at least 16 hr., at least 17 hr., at least 18 hr., at least 19 hr., at least 20 hr., at least 22 hr., or at least 24 hr.; and
(ii) at most 100 hr., at most 90 hr., at most 80 hr., at most 70 hr., at most 60 hr., at most 50 hr., at most 40 hr., at most 30 hr., at most 20 hr., at most 10 hr., at most 8 hr., at most 6 hr., at most 4 hr., or at most 2 hr.

A23. The method of any of paragraphs A21-A22, wherein, prior to the detecting the DLDMs, the method further includes at least one of:
(i) draining the sample solution from the given subarray;
(ii) removing a/the perimeter sealing structure from the microarray chip;
(iii) washing the microarray chip; and
(iv) drying the microarray chip.

B1. A kit of components configured to facilitate detection of a leak from a given subarray of a microarray chip, the kit comprising:
the microarray chip including:
(i) a substrate;
(ii) a plurality of subarrays formed on the substrate, wherein each subarray of the plurality of subarrays includes a plurality of test features, and further wherein each test feature of the plurality of test features includes anchored test molecules (ATMs), which are anchored to the substrate and define a predetermined anchored test oligonucleotide sequence;
(iii) a perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and
(iv) a leak detection region, wherein the leak detection region includes anchored leak detection molecules (ALDMs), which are attached to the substrate and define a predetermined anchored leak detection oligonucleotide sequence; and
dissolved leak detection molecules (DLDMs) that are configured to be dissolved within a sample solution for the given subarray and define a predetermined dissolved leak detection oligonucleotide sequence that is complementary to the predetermined anchored leak detection oligonucleotide sequence.

B2. The kit of paragraph B1, wherein the predetermined anchored test oligonucleotide sequence of each test feature differs from the predetermined anchor test oligonucleotide sequence of at least one of:
(i) at least one other test feature of the plurality of test features;
(ii) a majority of the other test features of the plurality of test features; and
(iii) all other test features of the plurality of test features.

B3. The kit of any of paragraphs B1-B2, wherein the predetermined anchored leak detection oligonucleotide sequence of the leak detection region differs from the predetermined anchored test oligonucleotide sequence of every test feature of the plurality of test features.

B4. The kit of any of paragraphs B1-B3, wherein the leak detection region is external the given subarray.

B5. The kit of any of paragraphs B1-B4, wherein:
(i) the given subarray is a first subarray;
(ii) the plurality of subarrays further includes a second subarray, which is adjacent to the first subarray; and
(iii) the leak detection region is positioned within the second subarray.

B6. The kit of paragraph B5, wherein the perimeter sealing structure is configured to fluidically isolate the first subarray from the second subarray.

B7. The kit of any of paragraphs B5-B6, wherein the leak detection region is a second leak detection region, and further wherein the microarray chip includes a first leak detection region that is positioned within the first subarray.

B8. The kit of paragraph B7, wherein the ALDMs are first ALDMs, wherein the predetermined anchored leak detection oligonucleotide sequence is a first predetermined anchored leak detection oligonucleotide sequence, wherein the first leak detection region and the second leak detection region both include the first ALDMs, and further wherein the first leak detection region and the second leak detection region both include second ALDMs, which are spaced-apart from the first ALDMs and define a second predetermined anchored leak detection oligonucleotide sequence that differs from the first predetermined anchored leak detection oligonucleotide sequence.

B9. The kit of paragraph B8, wherein the DLDMs are first DLDMs that define a first predetermined dissolved leak detection oligonucleotide sequence, and further wherein the kit includes second DLDMs that define a predetermined second dissolved leak detection oligonucleotide sequence that is complementary to the second predetermined anchored leak detection oligonucleotide sequence.

B10. The kit of any of paragraphs B1-B9, wherein each subarray includes a corresponding leak detection region, wherein a spatial arrangement of the plurality of subarrays defines a number of adjacent subarrays, and further wherein each corresponding leak detection region includes a number of distinct ALDM features that corresponds to, or is one greater than, the number of adjacent subarrays, wherein each ALDM feature of the number of distinct ALDM features:

(i) is spaced apart from each other ALDM feature of the number of distinct ALDM features; and (ii) includes corresponding ALDMs that define a corresponding predetermined anchored leak detection oligonucleotide sequence that differs from the predetermined anchored leak detection oligonucleotide sequence of each other ALDM feature.

B11. The kit of paragraph B10, wherein the kit further includes corresponding DLDMs that define a corresponding predetermined dissolved leak detection oligonucleotide sequence that is complementary to the corresponding predetermined anchored leak detection oligonucleotide sequence of only one ALDMs feature of the number of distinct ALDMs features and differs from a corresponding DLDMs of each other sample solution of the plurality of sample solutions.

B12. The kit of any of paragraphs B1-B11, wherein the leak detection region is at least one of:

(i) external to all subarrays of the plurality of subarrays;

(ii) positioned within a contact region between the perimeter sealing structure and the substrate; and (iii) positioned within an unwetted region of the microarray chip.

C1. A microarray chip, comprising:

a substrate;

a plurality of subarrays formed on the substrate, wherein each subarray includes a plurality of test features, and further wherein each test feature of the plurality of test features includes anchored test molecules (ATMs), which are anchored to the substrate and define a predetermined anchored test oligonucleotide sequence;

a perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and a leak detection region, wherein the leak detection region includes anchored leak detection molecules (ALDMs), which are attached to the substrate and define a predetermined anchored leak detection oligonucleotide sequence, wherein the leak detection region is at least one of:

(i) external to all subarrays of the plurality of subarrays; and (ii) positioned within a contact region between the perimeter sealing structure and the substrate.

C2. The microarray chip of paragraph C1, wherein the predetermined anchored test oligonucleotide sequence of each test feature differs from the predetermined anchor test sequence of at least one of:

(i) at least one other test feature of the plurality of test features;

(ii) a majority of the other test features of the plurality of test features; and (iii) all other test features of the plurality of test features.

C3. The microarray chip of any of paragraphs C1-C2, wherein the predetermined anchored leak detection oligonucleotide sequence of the leak detection region differs from the predetermined anchored test oligonucleotide sequence of every test feature of the plurality of test features.

C4. The microarray chip of any of paragraphs C1-C3, wherein the leak detection region is external the given subarray.

INDUSTRIAL APPLICABILITY

The kits, microarray chips, and methods disclosed herein are applicable to the healthcare and DNA sequencing industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A method of detecting a leak from a given subarray of a plurality of subarrays that are formed on a substrate and together define a microarray chip, the method comprising:

positioning, within the given subarray, a sample solution that includes:

(i) dissolved sample molecules (DSMs) that define a dissolved sample oligonucleotide sequence; and (ii) dissolved leak detection molecules (DLDMs) that define a predetermined dissolved leak detection oligonucleotide sequence; and detecting the DLDMs within a region of the microarray chip that is external to the given subarray;

wherein each subarray of the plurality of subarrays includes a corresponding leak detection region;

wherein the corresponding leak detection region includes anchored leak detection molecules (ALDMs), which are attached to the substrate and define a predetermined anchored leak detection oligonucleotide sequence that is complementary to the dissolved leak detection oligonucleotide sequence;

wherein a spatial arrangement of the plurality of subarrays defines a number of adjacent subarrays;

wherein each corresponding leak detection region includes a number of distinct ALDM features that is at least one of equal to the number of adjacent subarrays and one greater than the number of adjacent subarrays;

wherein each ALDM feature of the number of distinct ALDM features:

(i) is spaced apart from each other ALDM feature of the number of distinct ALDM features; and (ii) includes corresponding ALDMs that define a corresponding predetermined anchored leak detection oligonucleotide sequence that differs from the predetermined anchored leak detection oligonucleotide sequence of each other ALDM feature; and wherein the detecting the DLDMs includes detecting hybridization between the ALDMs and the DLDMs;

wherein the region of the microarray chip that is external to the given subarray is a first region of the microarray chip, and further wherein the detecting the DLDMs includes detecting the DLDMs in a second region of the microarray chip that is at least one of:

(i) external to all subarrays of the microarray chip;

(ii) positioned within a contact region between a perimeter sealing structure and the substrate; and (iii) positioned within an unwetted region of the microarray chip.

2. The method of claim 1, wherein each subarray of the plurality of subarrays includes:

(i) a perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and (ii) a plurality of test features, wherein each test feature of the plurality of test features includes anchored test molecules (ATMs), which are anchored to the substrate and define a predetermined anchored test oligonucleotide sequence.

3. The method of claim 2, wherein the predetermined anchored leak detection oligonucleotide sequence of the leak detection region differs from the predetermined anchored test oligonucleotide sequence of every test feature of the plurality of test features.

4. The method of claim 2, wherein:

(i) the given subarray is a first subarray;

(ii) the microarray chip further includes a second subarray, which is adjacent to the first subarray; and (iii) the leak detection region is positioned within the second subarray.

5. The method of claim 4, wherein the leak detection region is a second leak detection region, and further wherein the microarray chip includes a first leak detection region that is positioned within the first subarray.

6. The method of claim 5, wherein the ALDMs are first ALDMs, wherein the predetermined anchored leak detection oligonucleotide sequence is a first predetermined anchored leak detection oligonucleotide sequence, wherein the first leak detection region and the second leak detection region both include the first ALDMs, and further wherein the first leak detection region and the second leak detection region both include second ALDMs, which are spaced-apart from the first ALDMs and define a second predetermined anchored leak detection oligonucleotide sequence that differs from the first predetermined anchored leak detection oligonucleotide sequence.

7. The method of claim 6, wherein the sample solution is a first sample solution, wherein the DSMs are first DSMs that define a first dissolved sample oligonucleotide sequence, wherein the DLDMs are first DLDMs that define a first predetermined dissolved leak detection oligonucleotide sequence, and further wherein the positioning includes positioning, within the second subarray, a second sample solution that includes:

(i) second DSMs that define a second dissolved sample oligonucleotide sequence; and (ii) second DLDMs that define a predetermined second dissolved leak detection oligonucleotide sequence that is complementary to the second predetermined anchored leak detection oligonucleotide sequence.

8. The method of claim 7, wherein the detecting includes detecting a first leak from the first subarray to the second subarray, and further wherein the method includes detecting a second leak from the second subarray to the first subarray via detecting hybridization between the second DLDMs and the second ALDMs of the first subarray.

9. The method of claim 1, wherein the positioning includes positioning, within each subarray, a corresponding sample solution of a plurality of sample solutions, wherein the corresponding sample solution includes:

(i) corresponding DSMs; and (ii) corresponding DLDMs that define a corresponding predetermined dissolved leak detection oligonucleotide sequence that is complementary to the corresponding predetermined anchored leak detection oligonucleotide sequence of only one ALDM feature of the number of distinct ALDM features and differs from a corresponding DLDMs of each other sample solution of the plurality of sample solutions.

10. The method of claim 9, wherein the method further includes identifying the given subarray based, at least in part, on which corresponding DLDMs is detected during the detecting and within which subarray of the plurality of subarrays the corresponding DLDMs is positioned during the positioning.

11. The method of claim 1, wherein the positioning includes positioning, within each subarray, a corresponding sample solution of a plurality of sample solutions, wherein each corresponding sample solution includes:

(i) corresponding DSMs; and (ii) the same DLDMs.

12. The method of claim 1, wherein the DLDMs include attached fluorophores, and further wherein the detecting the DLDMs includes detecting fluorescence of the attached fluorophores within the region of the microarray chip that is external to the given subarray.

13. The method of claim 1, wherein the number of adjacent subarrays only includes subarrays that share at least one of a wall of a perimeter sealing structure of the microarray chip and a corner of the perimeter sealing structure.

14. The method of claim 1, wherein, for at least a subset of the plurality of subarrays, the number of adjacent subarrays includes eight adjacent subarrays.

15. The method of claim 1, wherein, for at least a subset of the plurality of subarrays, the number of adjacent subarrays is exactly eight adjacent subarrays.

16. A microarray chip, comprising:

a substrate;

a plurality of subarrays formed on the substrate, wherein each subarray includes a plurality of test features, and further wherein each test feature of the plurality of test features includes anchored test molecules (ATMs), which are anchored to the substrate and define a predetermined anchored test oligonucleotide sequence;

a perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and a leak detection region, wherein the leak detection region includes anchored leak detection molecules (ALDMs), which are attached to the substrate and define a predetermined anchored leak detection oligonucleotide sequence, wherein the leak detection region is at least one of:
  (i) external to all subarrays of the microarray chip; and
  (ii) positioned within a contact region between the perimeter sealing structure and the substrate.

17. A method of detecting a leak from a given subarray of a plurality of subarrays that are formed on a substrate and together define a microarray chip, the method comprising:
  positioning, within the given subarray, a sample solution that includes:
    (i) dissolved sample molecules (DSMs) that define a dissolved sample oligonucleotide sequence; and
    (ii) dissolved leak detection molecules (DLDMs) that define a predetermined dissolved leak detection oligonucleotide sequence; and
  detecting the DLDMs within a region of the microarray chip that is external to the given subarray;
  wherein the region of the microarray chip that is external to the given subarray is at least one of:
    (i) external to all subarrays of the microarray chip;
    (ii) positioned within a contact region between a perimeter sealing structure and the substrate; and
    (iii) positioned within an unwetted region of the microarray chip.

18. The method of claim 17, wherein the positioning includes positioning, within each subarray, a corresponding sample solution of a plurality of sample solutions, wherein each corresponding sample solution includes:
  (i) corresponding DSMs; and
  (ii) the same DLDMs.

19. The method of claim 17, wherein each subarray of the plurality of subarrays includes:
  (i) the perimeter sealing structure configured to form a fluid seal with the substrate, wherein the perimeter sealing structure and the substrate together define a fluid-receiving well of each subarray, and further wherein the perimeter sealing structure is configured to fluidically isolate each subarray from all other subarrays of the plurality of subarrays; and
  (ii) a plurality of test features, wherein each test feature of the plurality of test features includes anchored test molecules (ATMs), which are anchored to the substrate and define a predetermined anchored test oligonucleotide sequence; and
  wherein the microarray chip further includes a leak detection region, wherein the leak detection region includes anchored leak detection molecules (ALDMs), which are attached to the substrate and define a predetermined anchored leak detection oligonucleotide sequence that is complementary to the dissolved leak detection oligonucleotide sequence; and
  further wherein the detecting the DLDMs includes detecting hybridization between the ALDMs and the DLDMs.

* * * * *